(12) United States Patent
Li (10) Patent No.: US 6,604,421 B1
(45) Date of Patent: Aug. 12, 2003

(54) METHOD, TRANSDUCER WHEEL AND FLAW DETECTION SYSTEM FOR ULTRASONIC DETECTING RAILROAD RAILS

(76) Inventor: Gang Li, c/o Steellex Instrument Co., 1 Fourth Street Shangdi, 25 Road (e), Shangdi Information Industrial Base, Beijing 100085 (CN)

( * ) Notice: Subject to any disclaimer, the term of this patent is extended or adjusted under 35 U.S.C. 154(b) by 0 days.

(21) Appl. No.: 09/830,002
(22) PCT Filed: Oct. 23, 1998
(86) PCT No.: PCT/CN98/00257
§ 371 (c)(1),
(2), (4) Date: Jul. 6, 2001
(87) PCT Pub. No.: WO00/25126
PCT Pub. Date: May 4, 2000

(51) Int. Cl.$^7$ ................................................ G01N 29/04
(52) U.S. Cl. ........................................................ 73/636
(58) Field of Search ................................ 324/217, 534, 324/718; 702/39; 73/636, 597, 627

(56) References Cited

U.S. PATENT DOCUMENTS

| | | | |
|---|---|---|---|
| 4,165,648 A | 8/1979 | Pagano | |
| 4,334,602 A | * 6/1982 | Armour et al. | ......... 188/181 A |
| 4,468,966 A | 9/1984 | Bradshaw | |
| 4,487,071 A | 12/1984 | Pagano et al. | |
| 5,419,196 A | * 5/1995 | Havira et al. | .................. 73/623 |
| 5,578,758 A | * 11/1996 | Havira et al. | .................. 73/636 |

FOREIGN PATENT DOCUMENTS

| | | |
|---|---|---|
| CN | 1096459 | 12/1994 |
| JP | 3183945 | 8/1991 |
| JP | 9101288 | 4/1997 |

* cited by examiner

*Primary Examiner*—John E. Chapman
*Assistant Examiner*—James C. Kerveros
(74) *Attorney, Agent, or Firm*—Ladas & Parry (57) ABSTRACT

This invention relates to a nondestructive flaw detection method, especially an ultrasonic flaw detection method for detecting rail flaws, as well as the wheel transducer and flaw detection system for implementing the method. According to the method, a solid coupling medium couples ultrasonic waves. The wheel transducer according to the invention includes a tire made of ultrasonic wave permeable materials, probes combining ultrasonic emitter/receiver, a sliding plate and the means for reducing friction between the sliding plate and the bottom of the tire of the wheel transducer while flaw detection. The sliding plate is fixed on the fixed axle of the wheel transducer. The probes combining ultrasonic emitter/receiver are mounted on the sliding plate. While flaw detection, the sliding plate compels the wall of the tire of the wheel transducer to flat press on the surface of rails to be detected.

16 Claims, 6 Drawing Sheets

METHOD, TRANSDUCER WHEEL AND FLAW DETECTION SYSTEM FOR ULTRASONIC DETECTING RAILROAD RAILS

TECHNICAL FIELD

The invention relates to a nondestructive flaw detection method, especially an ultrasonic flaw detection method for detecting rail flaws, as well as the wheel transducer and flaw detection system for implementing the method.

BACKGROUND OF THE INVENTION

Figure 1:
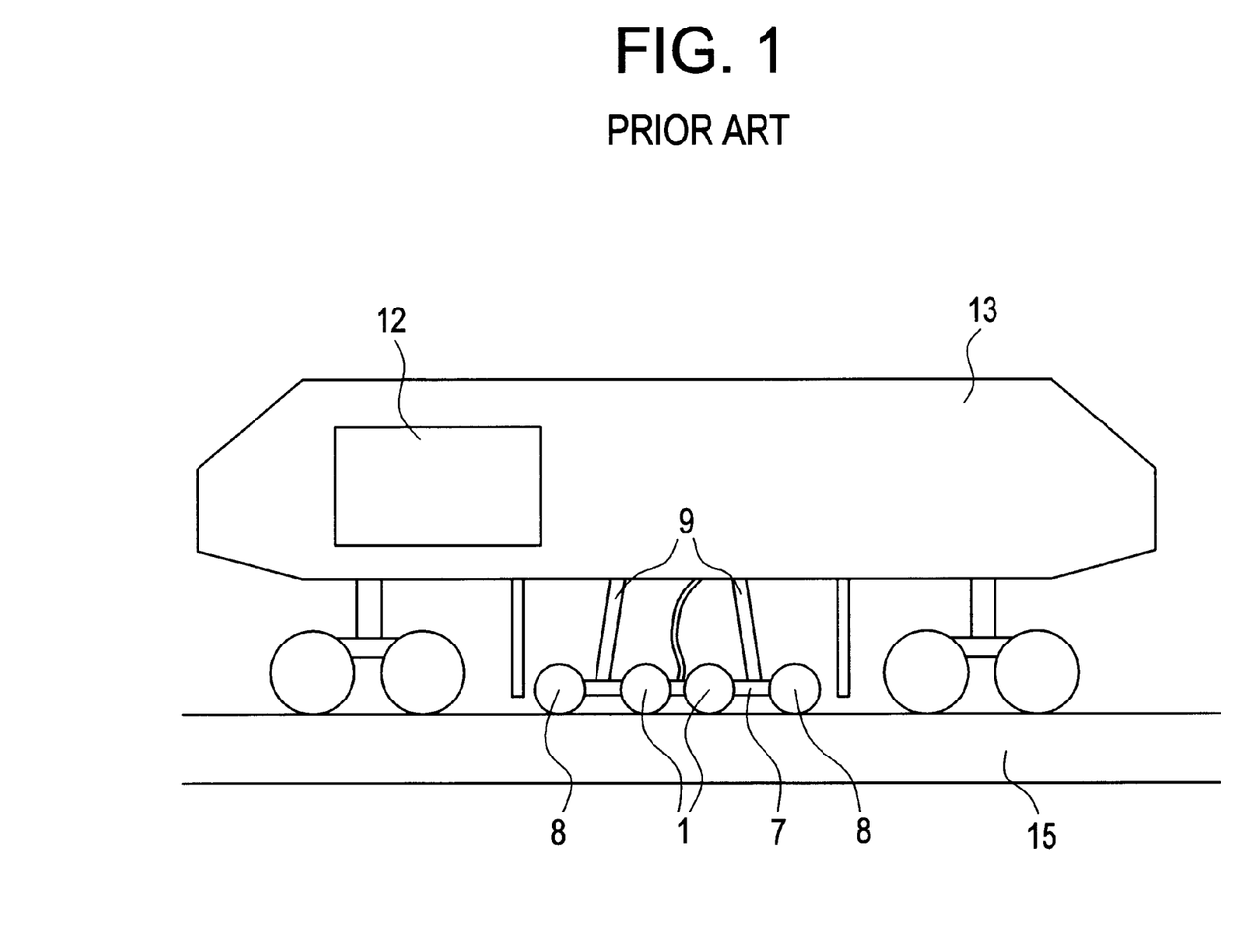
FIG. 1 is a schematic view of a wheel-type flaw detection system for detecting rail flaws in the prior art.
Figure 2A:
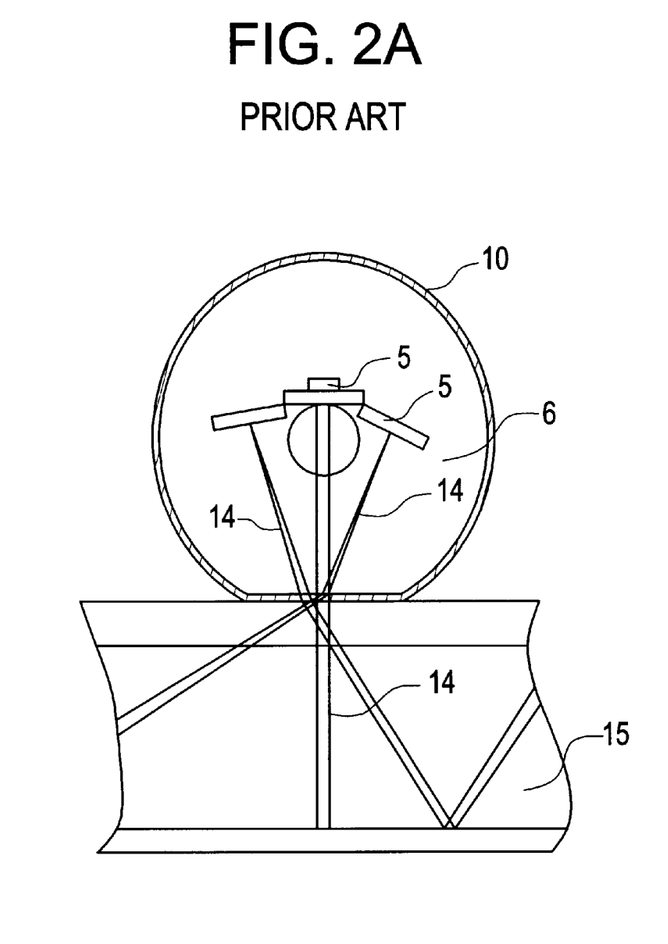
FIGS. 2(a) and 2(b) are respectively the front view and side view of the flaw detection system shown in FIG. 1.
Figure 2B:
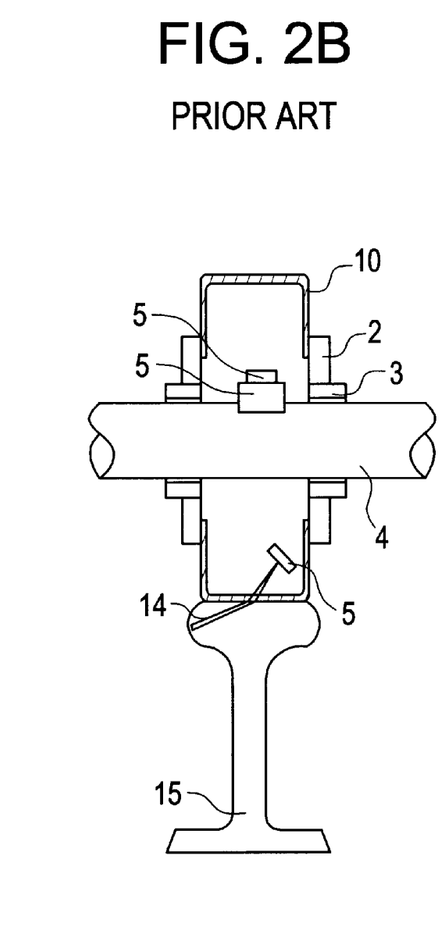
Figure 6A:
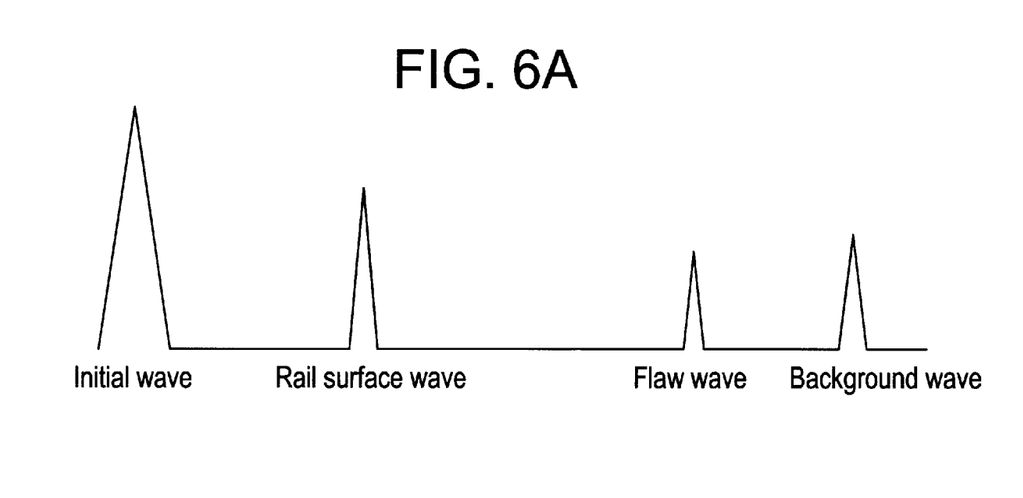
FIG. 6(a) is a schematic oscillogram for illustrating the principle of the ultrasonic flaw detection system for detecting rail flaws.

In the technical fields in which it is necessary to ensure high safety and high reliability, such as industries of defense, aerospace and railway communications, nondestructive flaw detection methods are broadly used in detecting various flaws possibly present in key elements or units. In the field of railway communications, the nondestructive flaw detection system should have high detecting precision and high detecting rate, and, at present; a wheel-type system that can continuously detect rail flaws is generally adopted. U.S. Pat. No. 4,487,071 disclosed such a flaw detection system which includes, as shown in FIG. 1, wheel transducers 1, detecting supports 7, guiding wheels 8 for guiding the detecting supports and detecting support links 9 which fix the detection system on a flaw detection car 13. Each of the wheel transducers 1 comprises a tire 10 made of sound wave permeable thin rubber and filled with coupling fluid 6 for transmitting sound wave, as shown in FIGS. 2(a) and 2(b). The wheel transducer 1 further comprises probes 5 functioning as ultrasonic emuitter/receiver. When detecting flaws, the probes 5 continuously emit ultrasonic pulse beams 14, which pass through the coupling fluid 6 and the tire 10 into the rail 15 to be detected. If no flaw is present in the rail, the beams 14 arrive at the bottom surface of the rail and are reflected to the probes, resulting in a background wave. If there is a flaw in the rail, a flaw wave is obtained before the background wave (as shown in FIG. 6(a)). The probes 5 receive the reflected echo signal and deliver it to a processing unit 12, which outputs continuous detection results.

However, said flaw detection system has the following main disadvantages. Firstly, because the distance from the, probes to the rail is relatively long, and the sound wave's propagation velocity in the coupling fluid is relatively small (approximately ⅕ of that in steel), the sound wave is delayed and when the detecting rate increases, the echo wave will progressively drop behind fori a certain distance and cannot be received correctly by the probes, which results in signal missing. Secondly, when the wheel transducer having thin-wall tire and internal coupling fluid rotates in high speed, the viscosity, tlie inertia of the internal coupling fluid and the weak elasticity of the external wall of the thin rubber tire lead to interfering force, and, as results, the wheel transducer cannot retain a planar coupling surface which is necessary for detecting operation. Accordingly, the emitting and reflecting of the ultrasonic sound wave are cumbered, or interfering reflecting surfaces occur, and the missing echo signals and interfering waves increase. Finally, in order to avoid vibrating of the wheel transducer, the detecting support must be yvery heavy (typically>1 ton) and very solid. Accordingly, when the detecting support moves in high speed, the great inertia force makes the detecting support not so easy to be guided and apt to derail, and, in turn, apt to be blocked under the detection car, which influences severely the running safety.

SUMMARY OF THE INVENTION

Therefore, an object of the invention is to provide an ultrasonic flaw detection method for detecting rail flaws using wheel transducers, as well as the wheel transducer and the flaw detection system for implementing the method, so that the echo signals are received correctly even in high speed flaw detection, with the missing echo signals significantly reduced, the interfering waves lowered, and the running safety considerably improved.

According to a first aspect of the invention, an ultrasonic flaw detection method for detecting rail flaws using wheel transducers is provided, comprising the following steps: generating continuous ultrasonic pulse beams; coupling the beams through coupling medium into the rail to be detected; detecting the echo signals of the beams reflected from the rail and processing said echo signals to determine whether there is any flaw in the rail. The method is characterized in that the coupling medium used in the coupling step is solid.

According to a second aspect of the invention, an ultrasonic wheel transducer for detecting rail flaws for implementing the above method is provided, comprising a tire made of ultrasonic wave permeable materials and probes functioning as ultrasonic emitter/receiver, characterized in that the wheel transducer further comprises a sliding plate and means for reducing friction between the sliding plate and the wall of the tire of the wheel transducer during flaw detection, wherein said sliding plate is fixed on the fixed axle of the wheel transducer, and said probes functioning as ultrasonic emitter/receiver are mounted on the sliding plate, and wherein, in the course of flaw detection, the sliding plate compels the wall of the tire of the wheel transducer to flat press on the surface of the rail to be detected.

Said means for reducing friction may be formed as follows: jetting holes are formed in the sliding plate, and when detecting flaws, coupling fluid of high pressure is jetted out of the jetting holes and forms a thin fluid film between the sliding plate and the wall of the tire of the wheel transducer. Said means for reducing friction may also be comprised of rollers or balls mounted on the sliding plate, said rollers or balls being pressed against the wall of the tire of the wheel transducer. The means for reducing friction may still also be as such: necessary small gap is maintained constantly between the sliding plate and the wall of the tire of the wheel transducer by means of automatic control techniques, so that the wheel transducer rolls smoothly on the rail.

According to a third aspect of the invention, it is provided a wheel-type ultrasonic flaw detection system for detecting rail flaws for implementing said method, comprising fixing means for mounting the system on the body of detection car and elevating means associated with the fixing means, characterized in that, the system further comprises wheel transducers mounted on the elevating means through a fixing base, said wheel transducer comprises a tire made of ultrasonic sound wave permeable materials, probes functioning as ultrasonic emitter/receiver, a sliding plate and means for reducing friction between the sliding plate and the wall of the tire of the wheel transducer in course of flaw detection, wherein the sliding plate is fixed on the fixed axle of the wheel transducer, the probes functioning as ultrasonic emitter/receiver are mounted on the sliding plate, and, in course of flaw detection, the sliding plate compels the wall of the tire of the wheel transducer to flat press on the surface of the rail to be detected.

According to the above solutions, the ultrasonic wave beam directly passes through the solid sliding plate into the rail, so that the delay of the ultrasonic wave occurring when using coupling fluid is considerably reduced, and the echo signals are received correctly even in high speed detection. Additionally, since the coupling surface necessary for detecting is formed by the wheel transducer's tire which is compelled by the sliding plate to flat press on the surface of the rail to be detected, the coupling surface can be kept planar even in high speed detection, so that the opportunities of missing echo signals and appearing interfering waves are eliminated, at least reduced. Moreover, according to the invention, the detecting support is no longer necessary and running safety is improved significantly.

DETAILED DESCRIPTION OF PREFERRED EMBODIMENTS OF THE INVENTION

Figure 3:
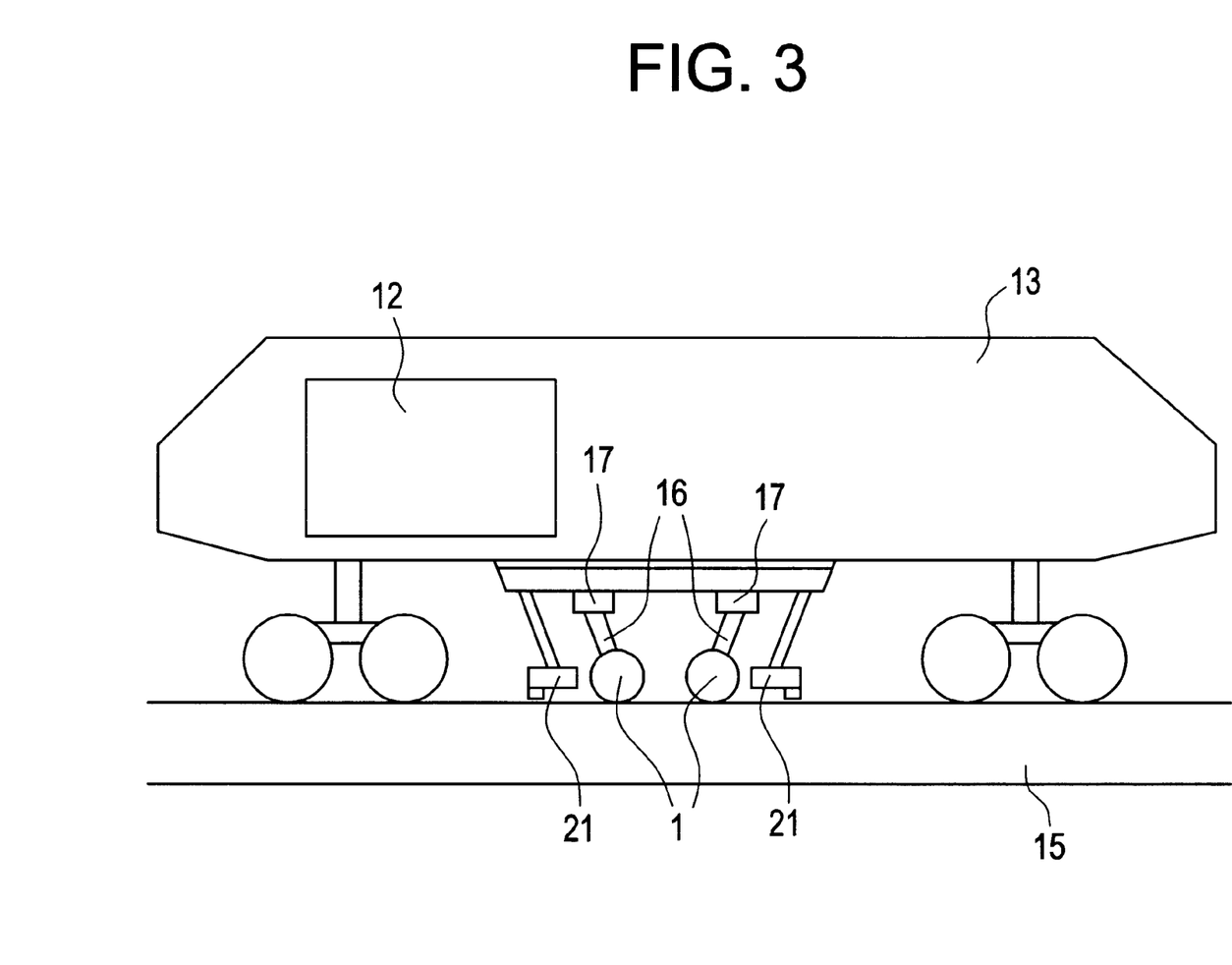
FIG. 3 is a schematic view of an ultrasonic flaw detection system for detecting rail flaws according to one embodiment of the invention, which is mounted on a detection car.

Now referring to FIG. 3, the ultrasonic flaw detection system for detecting rail flaws according to the invention comprises four wheel transducers 1 of the invention. When mounted on a detection car 13, two of the wheel transducers are positioned on one rail, and the other two of the wheel transducers are positioned on another rail. Each of the wheel transducers 1 is associated to the detection car 13 through a fixing base 25, an automatic elevating servo mechanism 16 and an automatic centering servo mechanism 17 (as shown in FIG. 5).

Figure 4A:
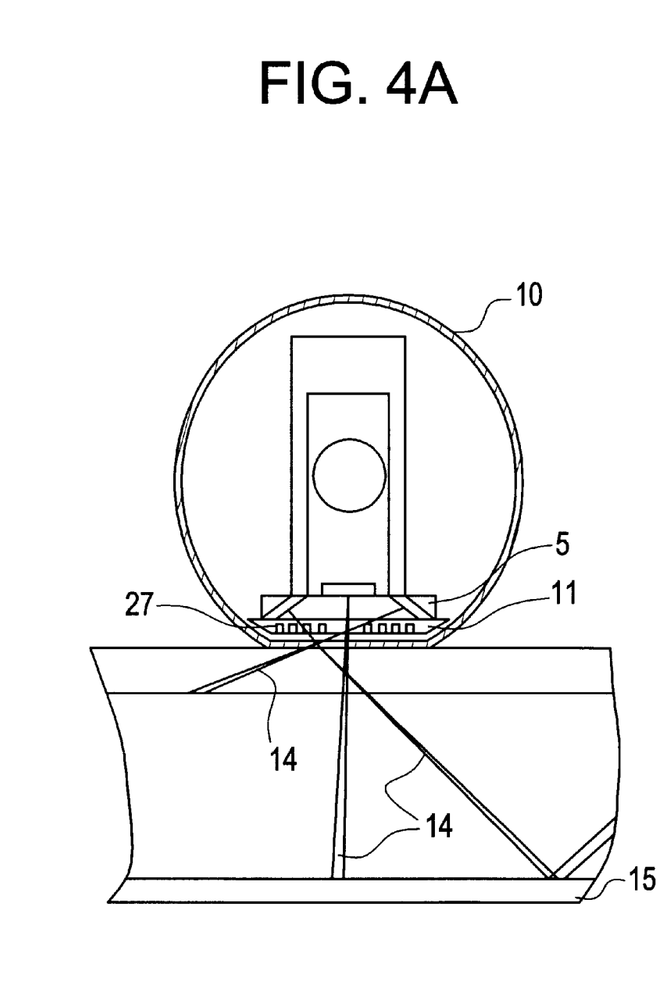
FIGS. 4(a) and 4(b) are respectively the front view and side view of an ultrasonic wheel transducer for detecting rail flaws according to the invention.
Figure 4B:
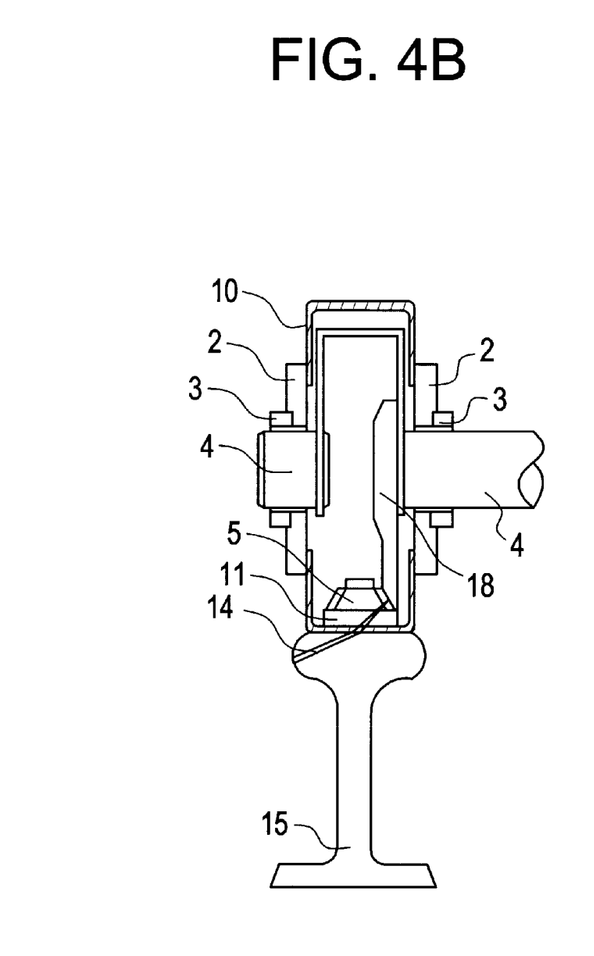

The wheel transducer 1 comprises an annular tire 10 made of ultrasonic wave permeable thin rubber and is mounted on the rotating axle 3 of the wheel transducer through its hub 2. The tire 10 is preferably made of synthesized ultrasonic wave permeable rubber of the type of polyamine. To reduce the waste of ultrasonic wave, it is necessary to make the tire wall very thin. On the inner flange of the hub 2 is disposed a seal ring to prevent the coupling fluid from leaking. In the wheel transducer 1, a rigid sliding plate is mounted on a pressing assembly 18, which is in turnmfixed on the fixed axle 4 of the wheel transducer. On one side of the sliding plate 11 opposite to the tire wall are mounted probes 5 functioning as ultrasonic emitter/receiver. The emission of the probes is oriented to the detecting surface of the wheel wall. One vertical probe is sufficient for detecting horizontal flaws or pore flaws, etc. As to complex flaws, more probes are necessary to detect transversal and longitudinal flaws. Therefore, to improve the reliability of flaw detection, each sliding plate can be equipped with probes along three dimensions so that horizontal, longitudinal and transversal flaws could be detected simultaneously. Furthermore, as the sliding plate is relatively long, a plurality of groups of probes may be mounted on it, so that not only the reliability of flaw detection is improved, but also the following problem is solved: different probes disposed slantwise in same wheel transducer are unable to emit/receive ultrasonic wave beams between each other. Therefore, the flaw detection may be realized by a single wheel transducer. While detecting, the pressing assembly 18 passes very high pressure to the sliding plate 11, which compels the thin tire wall of the wheel transducer to flat press on the surface of the rail 15 to be detected, so that the probes 5 are coupled directly with the rail surface through the thin tire wall made of ultrasonic wave permeable rubber, without any ultrasonic wave delay within the wheel transducer. In the sliding plate 11 are distributed fluid jetting holes 27, which are connected through conduits to a pipe 23 supplying high pressure coupling fluid. In flaw detection, high pressure coupling fluid is jetted from the fluid jetting holes 27 so as to form a fluid film between the sliding plate 11 and the tire wall, so that the sliding plate is floated over the tire wall, the resistance being small. In this way, the sliding plate presses the tire wall flat and floats on it, which ensures the reliable coupling and smoothness of the wheel transducer 1. At the same time, the uniformity of fluid floating force can completely eliminate the warping of the coupling surface that may be caused by the non-uniform elasticity of the tire wall, and eliminate undesired reflecting surfaces that may generate interfering waves while detecting in high speed, so that the emitting and receiving of the ultrasonic waves are smooth and the signals obtained are stable.

The sliding plate 11 is made of stainless steel. On the side pressing against the tire wall, the two ends of the sliding plate in the running direction of the detection car are preferably tapered in the form of an upward arc, so that the thin wall tire 10 rotates smoothly and has its passing ability on rails improved. Moreover, the distribution of the fluid jetting holes in the sliding plate 11 is preferably determined based on the distribution of the interaction force between the tire wall of the wheel transducer and he sliding plate. In particular, when the sliding plate slides, the non-uniformity of the interaction force between the tire wall of the wheel transducer and the sliding plate results in the sliding plate suffering relatively great resistance at its two ends in the running direction. Accordingly, said two ends may be provided with fluid jetting holes with relatively high density.

Figure 5:
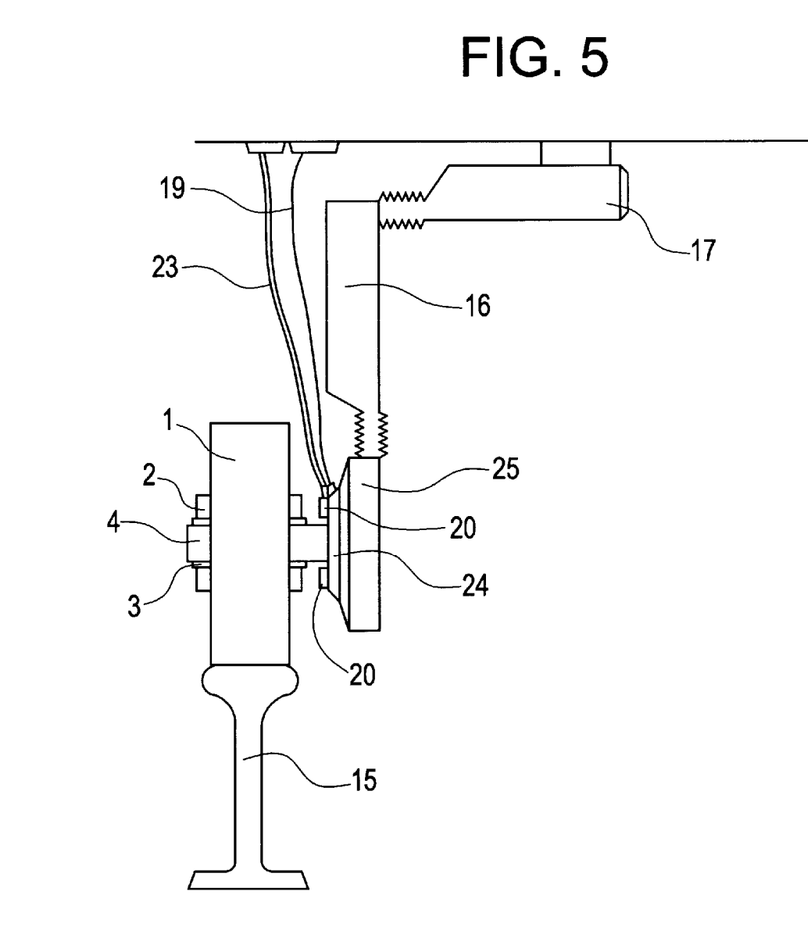
FIG. 5 is a partial schematic view of an ultrasonic flaw detection system for detecting rail flaws according to one embodiment of the invention.

Now referring to FIG. 5, the automatic elevating servo mechanism 16 and the pressing assembly 18 are used together to lift or lower the wheel transducer 1 and to apply pressure on the rail 15. Within said mechanism and assembly there are provided sensors for sensing velocity, pressure and position and regulators. The pressing assembly 18 adjusts the pressure applied on the sliding plate to be proportional to the detecting velocity. Said mechanism and assembly can automatically adjust and compensate the variations in pressure and vertical positions of the wheel transducer and the sliding plate caused by the up-and-downs of the rail, and ensure that the wheel transducer and the sliding plate should not vibrate and couple with the rail surface with high reliability during full-speed detection. Alternatively, the pressing assembly 18 may be omitted and the sliding plate 11 may be fixed directly on the fixed axle of the wheel transducer 1. As shown in FIG. 3, during flaw detection, the automatic elevating servo mechanism 16 is preferably slanted in the running direction of the detection car, so that the wheel transducers may be operated in two dimensions and the distance between the two wheel transducers on same rail may be adjusted automatically. In this way, tdie wave beam emitting/receiving of a pair of tilted probes among the combined probes of the sliding plates of the two wheel transducers may be matched with each other. If said emitting and receiving are matched correctly, the amplitude of received echo signal is the largest. Said echo signal is delivered to the automatic elevating servo mechanism 16 so that the latter automatically locks the distance between wheels in real time.

Some probes of the combined probes 5 are dedicated to detecting the flaws in the rail web and the pore flaws in the bolts used in the rail. If the positions of the probes shift, said important signals will be missed. The automatic centering servo mechanism 17 continuously detects the signals of the vertical probes of the combined probes. When the vertical probes are positioned in the middle, the wave beam passes successfully through the web to the rail bottom, and the amplitude of the reflected echo wave is the largest. When the probes shift even slightly, the adjusting means provided in the automatic centering servo mechanism 17 will adjust the wheel transducer to and lock it in the middle position in real time according to the variation of the amplitude of the echo wave, and the high precise auto-tracking of the wheel transducer is ensured. Alternatively, the automatic centering servo mechanism 17 may be omitted and replaced by manual centering.

As shown in FIG. 5, the fixed axle base 24 of wheel transducer and the fixing base 25 of the automatic elevating servo mechanism are fixed using bolts 20 with predetermined tension. An auto-retracting cable wire 19 connects the fixed axle base 24 of the wheel transducer to the detection car. When the wheel transducer suffers unexpected impact, if the impact force exceeds said predetermined tension of said bolts 20, said bolts 20 will break automatically and the auto-retracting cable wire 19 will pull the instantly fallen wheel transducer up to the bottom of the detection car, guaranteeing the running safety. After the wheel transducer has fallen off, the fixing base on the automatic elevating servo mechanism remains perfect, on which spare wheel transducer can be mounted again. Therefore, the ultrasonic flaw detection system for detecting rail flaws of the invention also provides the assembly with the capability of being repaired in field. Furthermore, protecting plates 21 (as shown in FIG. 3) may be provided for keeping the fallen wheel transducer out of the rail, improving the running safety further Table 1 illustrates the main specifications of the ultrasonic flaw detection system for detecting rail flaws according to the invention, compared with those of the flaw detection system disclosed in U.S. Pat. No. 4,487,071.

TABLE 1

| | THE INVENTION | U.S. PAT. NO. 4,487,071 |
| --- | --- | --- |
| DETECTING RATE | ≧80 km/h | ≦40 km/h |
| REPEATING FREQUENCY OP ULTRASONIC PULSE | 500–5000/s | 500–2000/s |
| TIME FOR FLAW DISTINGUISHING | ≦200 microseconds | ≦400 microseconds |
| ADJUSTING PRECISION OF AUTO-SERVO MECHANISM IN ALL DIRECTIONS | ≦1 mm | NONE |
| AUTO-TRACKING ON RAIL | YES | NO |
| TYPES OF FLAWS DISTINGUISHABLE | Core Flaw and Fracture of Bolt Hole | Fracture of Bolt Hole, but poor for core flaw detecting |
| PROTECTING DEVICE | YES | NO |

The following is the process of a high speed rail flaw detection using the ultrasonic flaw detection system for detecting rail flaws according to the invention. The automatic elevating servo mechanism 16 puts down the wheel transducer 1 on the rail 15. The pressing assembly 18 applies pressure on the sliding plate 11 within the wheel transducer 1 and compels the coupling surface of the wheel wall to flat press on the rail surface. The pipe 23 supplying high pressure coupling fluid supplies high pressure fluid to the fluid jetting holes 27 in the sliding plate 11 and makes the latter floated. The probes 5 functioning as ultrasonic emitter/receiver emit ultrasonic pulses. The automatic elevating servo mechanism 16 adjusts automatically the distance between the two wheel transducers on same rail, making a pair of detecting pulses of the two wheel transducers matched with each other. The centering servo mechanism 17 adjusts the middle position of the probes 5 functioning as ultrasonic emitter/receiver to make the wheel transducer positioned in the middle. So far, the flaw detection system is ready to work. While detecting, the detection car 13 moves, the flaw detection system is controlled automatically by a computer, and the pressure applied by the sliding plate and the frequency of the continuously emitted ultrasonic pulses are proportional to the detecting rate to obtain desired detecting precision. Each time the probes 5 functioning as ultrasonic emitter/receiver emit a pulse, the computer analyzes the echo wave instantly, distinguishes the type of the flaw, the depth and the size of the flaw, and, together with velocity/distance sensors, determines the position of the flaw. If the transducer suffers undesired impact, the bolts 20 with predetermined tension will break automatically, the protecting plates will keep the fallen wheel transducer out, and the auto-retracting cable wire 19 will pull the fallen wheel transducer up, so that the running safety is guaranteed.

Some test results are given below about the ultrasonic sound wave flaw detection system for detecing rail flaws according to the invention.

Figure 6B:
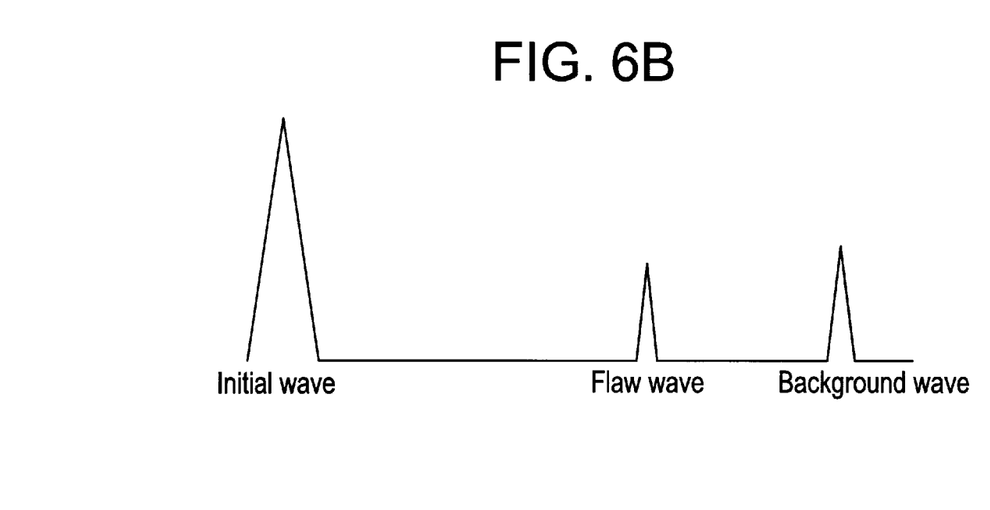
FIG. 6(b) is a schematic oscillogram for illustrating one example of the invention.

The ultasonic wave flaw detection system for detecting rail flaws according to the invention is mounted on a support, and the wheel transducers are placed on a rail formed as a circle with a diameter of 3 m. In the web of the trail is drilled a pore with diameter of 3 mm, and the circular rail moves in a linear velocity of 0–80 km/h. With such velocity of the circular rail, the detecting computer can always give out an oscillogram of flaw echoes as shown in FIG. 6(b).

What is claimed is:

1. An ultrasonic wheel transducer for detecting rail flaws comprising a tire made of ultrasonic wave permeable materials and probes functioning as an ultrasonic emitter/receiver, wherein the wheel transducer further comprises:

a sliding plate fixed to the fixed axle of the wheel transducer, said probes being mounted on the sliding plate, and, during the course of flaw detection, the sliding plate compelling the wall of the tire of the wheel transducer to press flat on the surface of the rail to be detected; and means for reducing friction between the sliding plate and the wall of the tire of the wheel transducer in the course of flaw detection.

2. An ultrasonic wheel transducer for detecting rail flaws according to claim 1, wherein the wheel transducer further comprises a pressing assembly, said sliding plate being fixed to the fixed axle of the wheel transducer through said pressing assembly.

3. An ultrasonic wheel transducer for detecting rail flaws according to claim 2, wherein within said pressing assembly there are provided sensors for sensing velocity, pressure and position and regulators, for adjusting the pressure applied on the sliding plate to be proportional to the detecting velocity.

4. An ultrasonic wheel transducer for detecting rail flaws according to claim 1, wherein said means for reducing friction comprises jetting holes formed in the sliding plate, and, while detecting flaws, coupling fluid of high pressure is jetted out of the jetting holes and forms a thin fluid film between the sliding plate and the wall of the tire of the wheel transducer.

5. An ultrasonic wheel transducer for detecting rail flaws according to claim 4, wherein the distribution of the fluid jetting holes in the sliding plate 11 is determined based on the distribution of the interaction force between the tire wall of the wheel transducer and the sliding plate.

6. An ultrasonic wheel transducer for detecting rail flaws according to claim 1, wherein said means for reducing friction comprises rollers or balls mounted on the sliding plate, said rollers or balls being pressed against the wall of the tire of the wheel transducer.

7. An ultrasonic wheel transducer for detecting rail flaws according to claim 1, wherein said means for reducing friction comprises a small gap between the sliding plate and the wall of the tire of the wheel transducer, maintained constant by automatic control means so that the wheel transducer rolls smoothly on the rail.

8. An ultrasonic wheel transducer for detecting rail flaws according to claim 1, wherein said sliding plate is rigid.

9. An ultrasonic wheel transducer for detecting rail flaws according to claim 1, wherein said sliding plate is tapered in the form of an upward arc on the side pressing against the wall of the tire, at its two ends in the running direction of the detection car, so that the wheel transducer rolls smoothly and the wheel transducer's passing ability on rails is improved.

10. An ultrasonic wheel transducer for detecting rail flaws according to claim 1, wherein said tire of the wheel transducer is made of polyamine type of synthesized ultrasonic wave permeable rubber.

11. A wheel-type ultrasonic flaw detection system for detecting rail flaws comprising fixing means for mounting the system on the body of a detection car and elevating means associated with the fixing means, wherein the system further comprises at least one wheel transducer including a tire made of ultrasonic wave permeable materials and probes functioning as an ultrasonic emitter/receiver, a sliding plate fixed to the fixed axle of the wheel transducer, said probes being mounted on the sliding plate, and, during the course of flaw detection, the sliding plate compelling the wall of the tire of the wheel transducer to press flat on the surface of the rail to be detected, and means for reducing friction between the sliding plate and the wall of the tire of the wheel transducer during the course of flaw detection, said wheel transducer being mounted on said elevating means through a fixing base of said elevating means.

12. A wheel-type ultrasonic flaw detection system for detecting rail flaws according to claimn 11, wherein said wheel transducer is associated with said fixing base of said elevating means through bolts with a predetermined tension, and the system further comprising an auto-retracting cable wire associated with said wheel transducer, wherein, when the wheel transducer suffers unexpected impact, said bolts will break automatically and the auto-retracting cable wire will pull the fallen wheel transducer up if the impact force exceeds said predetermined tension of said boats.

13. A wheel-type ultrasonic flaw detection system for detecting rail flaws according to claim 12, wherein the system further comprises protecting plates for keeping said fallen wheel transducer out of the rail.

14. A wheel-type ultrasonic flaw detection system for detecting rail flaws according to claim 11, wherein said fixing means includes an automatic centering servo mechanism for locking said wheel transducer in a middle position in real time and realizing the high precise auto-tracking of the wheel transducer on the rail.

15. A wheel-type ultrasonic flaw detection system for detecting rail flaws according to claim 11, wherein said elevating assembly includes an automatic elevating servo mechanism for auto-adjusting and compensating the variations in pressure and in the vertical position of the wheel transducer and the sliding plate caused by the up-and-down movement of the rail during high speed detecting.

16. A wheel-type ultrasonic flaw detection system for detecting rail flaws according to claim 15, wherein said automatic elevating servo mechanism is slanted in the running direction of the detection car, so that the wheel transducer may be operated in two dimensions.

* * * * *